United States Patent [19]
Wolvek et al.

[11] 3,934,592
[45] Jan. 27, 1976

[54] SUTURE BRIDGE

[75] Inventors: Sidney Wolvek, Brooklyn; Sol Sobel, Manhasset Hills, both of N.Y.

[73] Assignee: Technibiotics, Inc., Brooklyn, N.Y.

[22] Filed: Mar. 14, 1974

[21] Appl. No.: 451,305

[52] U.S. Cl. ............................................. 128/335
[51] Int. Cl.² ......................................... A61B 17/08
[58] Field of Search ............ 128/334 R, 335, 85, 84, 128/86–88, 92–96, 336, 337, 132, 132 R, 155, 156–157, 171, 327, 346, 154

[56] References Cited
UNITED STATES PATENTS

| | | | |
|---|---|---|---|
| 1,852,098 | 4/1932 | Anderson | 128/335 |
| 2,199,025 | 4/1940 | Conn | 128/335 |
| 2,223,006 | 11/1940 | Laub | 128/335 |
| 2,520,436 | 8/1950 | Russell | 128/132 R |
| 3,473,528 | 10/1969 | Mishkin et al. | 128/335 |
| 3,695,271 | 10/1972 | Chodorow | 128/335 |
| 3,789,851 | 2/1974 | LeVeen | 128/335 |

*Primary Examiner*—Robert W. Michell
*Assistant Examiner*—Rick Opitz
*Attorney, Agent, or Firm*—Darby & Darby

[57] ABSTRACT

An assembly of bridges for retention sutures to be spaced along the length of a surgical incision, each bridge having an arched configuration so as to be spaced from the incision so that the healing of the wound is facilitated while affording a physician access to the incision. The ends of each bridge do not contact the skin but are associated with respective ones of a pair of flat mounting strips positioned on either side of the incision which distribute the pressure exerted by the bridge ends from the sutures evenly over a relatively large area.

11 Claims, 9 Drawing Figures

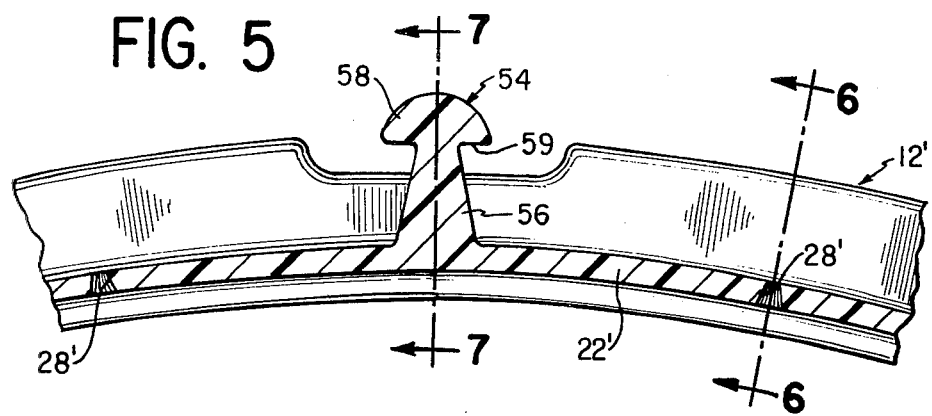
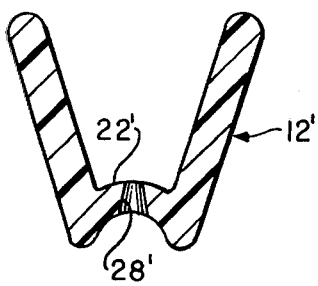
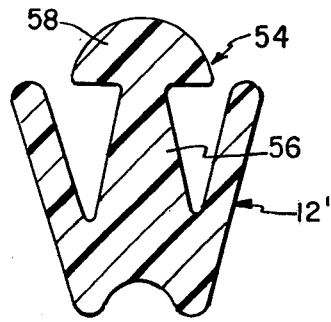
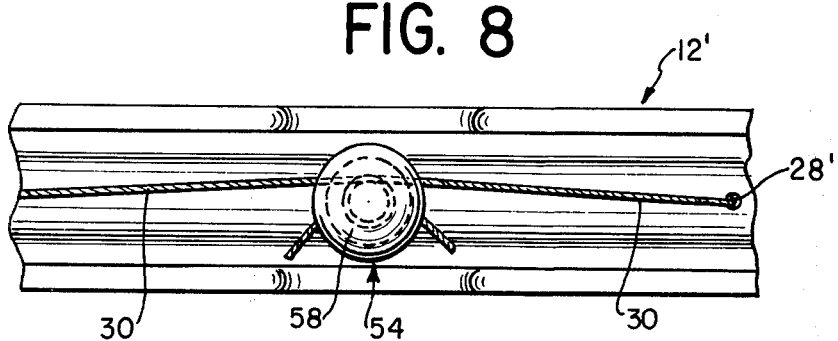
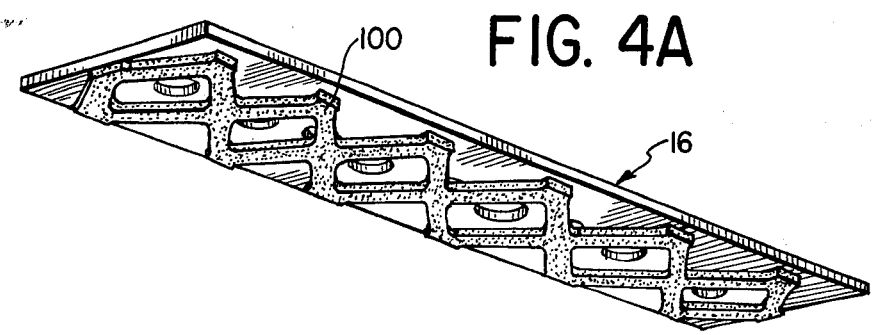

SUTURE BRIDGE

BACKGROUND OF THE INVENTION

This invention relates generally to bridges for retention sutures and, more particularly, to suture bridges which are spaced from the incision and which distribute pressure over a relatively large area adjacent the incision.

During surgical operations, particularly in the abdominal region, large incisions are frequently made. In order to promote the healing of these incisions, one or more retention sutures are provided along the length of the wound. A curved needle draws the suture thread down through the skin and layers of tissue on one side of the incision and then upwardly through the same layers piercing the skin on the opposite side of the incision. The two ends of the suture extending from the skin on either side of the incision are joined under tension thereby drawing the tissue together to promote healing.

Various bridging devices have been proposed to prevent the suture thread from being impressed into the skin and under-lying tissues when the suture is formed due to the transverse tension exerted on the incision by suture thread. One current technique in use comprises passing the ends of the suture thread through opposite ends of a length of plastic tubing which may have a telescoping construction so that its length may be varied to approximate the distance between the exit points of the suture thread from the body. However, although the pressure of the suture thread is somewhat more widely distributed over the skin in the vicinity of the incision than is the case where no tube is employed, the tube overlies and contacts the skin and the incision and does not necessarily prevent necrosis. Various other bridging elements have been used to provide fastening points for retention sutures. Wide plastic strips having a plurality of spaced openings such as that shown in U.S. Pat. No. 3,650,274, granted March 21, 1972, have been suggested. However, the incision becomes inaccessible since the bridge maintains contact with the skin along its entire length. Arch-type bridges wherein the bridge ends contact the skin in localized areas on either side of the incision, such as that shown in U.S. Pat. No. 3,695,271 granted Oct. 3, 1972, while alleviating pressure in the immediate vicinity of the incision, concentrate the pressure beneath the points of contact of the bridge ends.

Thus, it is seen that a dual problem exists with retention suture bridges currently used, namely, excessive pressure on the skin in the vicinity of the incision and lack of accessibility to the incision itself while the bridge is in position.

SUMMARY OF THE INVENTION

Accordingly, one object of the present invention is to provide a new and improved bridge assembly for retention sutures.

Another object of the present invention is to provide a new and improved bridge assembly which reduces the pressure on the skin resulting from its placement in the vicinity of the incision.

Still another object of the present invention is to provide a retention suture bridge of the above type which allows for free accessibility to all parts of the incision and to the area surrounding it.

Briefly, in accordance with the invention, these and other objects are attained by providing a pair of elongate, flexible strips preferably formed of a plastic material, each strip to be located on a respective side of an incision substantially parallel to it. Each strip has a plurality of openings formed along its length which mount the respective ends of an arch-shaped bridge. A number of bridges may be located along the length of the incision mounted in the same pair of strips. Thus, the pressure exerted by the ends of each bridge is transmitted to the long strips which distribute it evenly along its entire area while the arch construction permits free access to the area immediately surrounding the incision. The flexibility of the strip allows for compensatory distribution of pressure during breathing, coughing, etc.

DESCRIPTION OF THE DRAWINGS

FIG. 4A is a perspective view of a pressure distribution member with an expanded foam layer fixed to one of its surfaces;

FIG. 5 is an elevation view in section of a portion of another embodiment of a bridge;

FIG. 6 is a sectional view of the bridge taken along line 6—6 of FIG. 5;

FIG. 7 is a sectional view of the bridge taken along line 7—7 of FIG. 5; and

FIG. 8 is a plan view of a portion of a bridge and associated suture.

DESCRIPTION OF THE PREFERRED EMBODIMENTS

Figure 1:
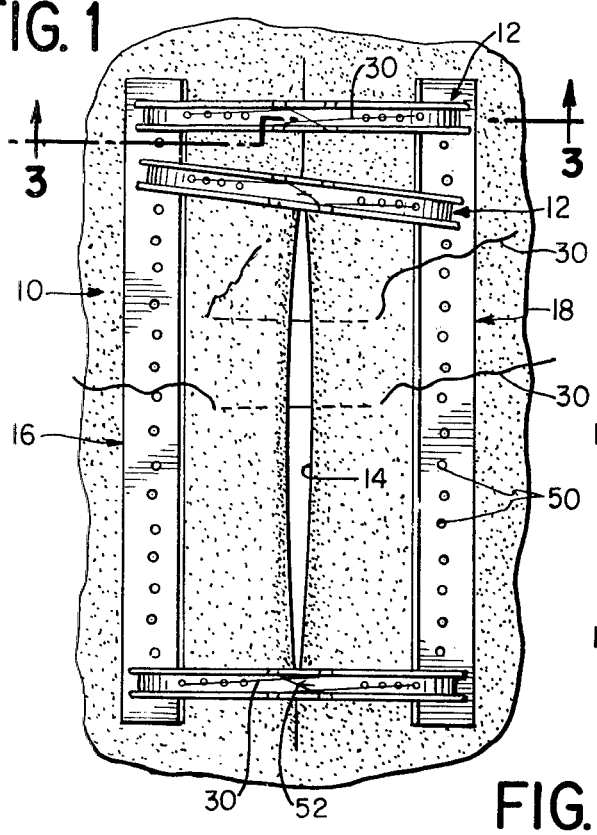
FIG. 1 is a plan view of the bridge assembly of the present invention illustrated during the suturing of an incision.
Figure 3:
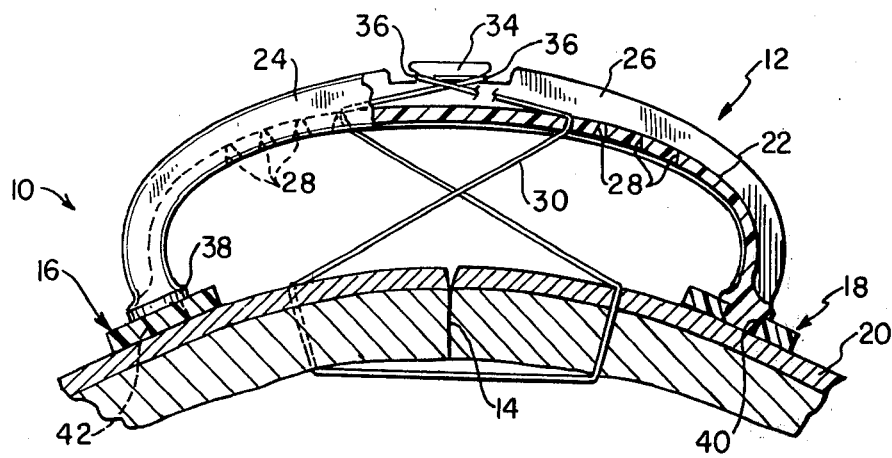
FIG. 3 is a front view in partial section of the bridge assembly along lines 3—3 of FIG. 1.

Referring now to the drawings wherein like reference characters designate identical or corresponding parts throughout the several views, the bridge assembly, generally denoted as 10, includes at least one bridge 12 (three shown in FIG. 1) which spans an incision 14 in a substantially transverse manner and a pair of pressure distributing members 16 and 18. As best seen in FIG. 3, the ends of a bridge 12 are fastened to respective pressure distributing members which themselves rest upon the skin 20 of the patient whose incision is being sutured. Referring to FIG. 1, it is understood that as more suture loops are sewn to close the incision, an equal number of bridges will be added to the assembly along the length of the incision 14.

Figure 4:
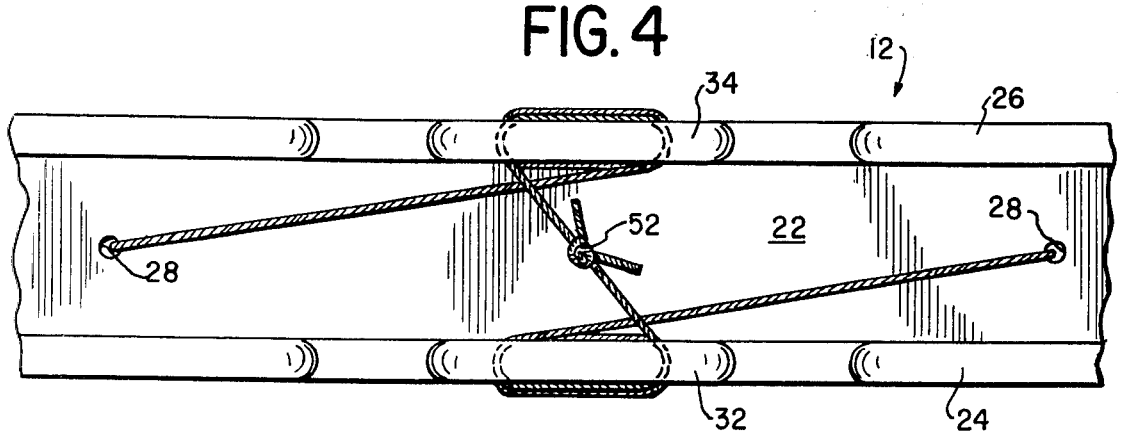
FIG. 4 is a plan view of a portion of a bridge and associated suture thread.

Referring to FIGS. 3 and 4, the suture bridge 12 comprises a generally U-shaped member preferably molded of a relatively rigid thermoplastic material. The bridge also preferably has a substantially U-shaped cross section defined by a bottom wall 22 having an arched cross section (similar to the one shown in FIG. 6) and a pair of side walls 24, 26 formed along its peripheral edges. A plurality of spaced apertures 28 are formed in bottom wall 22 on both sides of the apex of the bridge through which suture thread 30 may be passed as will be described in greater detail below. As described below in connection with FIG. 6, it is desirable to form bottom wall 22 with a generally arch-shape construction and with apertures 28 formed having a tapered construction to facilitate the passing of the suture thread through the apertures. A pair of posts 32, 34 are formed in bridge side walls 24, 26 respectively, each post having a pair of opposed notches 36 which facilitate securing the end portions of the suture thread 30 to the bridge after they have been threaded through apertures 28. The bottom and side walls of bridge 12 merge together into substantially circularly shaped ends 38, 40 each having an enlarged diameter relative to the bridge. A pin 42 extends from each end which is receivable within a particular opening formed in a pressure distributing member described below.

Figure 2:
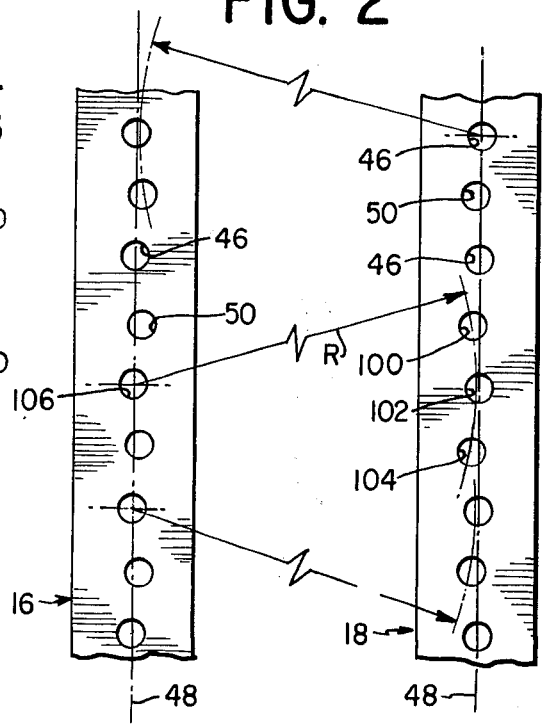
FIG. 2 is a plan view of the pressure distribution members of the assembly.

The pressure distributing members 16, 18 comprise a pair of relatively flat, flexible plastic strips of approximately the same length as the particular incision with which they are used. Each pressure distributing member (hereinafter referred to as pressure strips) has a plurality of openings, generally denoted as 44, which extend substantially along the entire length of the strip. Openings 44 are of approximately the same size as pins 42 so that a pin may be snugly received in a particular opening. Referring to FIG. 2, it is seen that the centers of a first set of alternate openings 46 define a longitudinal axis 48 on each strip. The other or second set of alternate openings 50 in the preferred embodiment are uniformly spaced a predetermined distance to one side of axis 48 for a reason which will become clear when the operation of the bridge assembly is described below. Although the structure of the pressure distributing members is preferred as described above, it is understood that the essential characteristics of these members are that they present a surface area relatively greater than the area of a bridge end and that some means are provided to fasten a bridge end to it. Thus other shapes and sizes of these members are possible within the scope of this invention.

The operation of the bridge assembly will now be described. When an incision such as incision 14 (FIG. 1) is about to be closed after completion of surgery, a pair of pressure strips 16, 18 are placed on the skin on opposite sides of and generally parallel to incision 14. It is usually the case that the bridge assembly will be situated on the skin for an extended length of time, i.e. up to two weeks. Under these circumstances, it is desirable to interpose a layer of expanded foam between the strip and the skin to assure that the skin directly beneath the strip will have access to air. As shown in FIG. 4A, the foam 100 might be adhesively fastened on the underside of each plate 16. Alternatively, the foam layer might be supplied separately from the plate. The surgeon then threads the suture thread 30 through the incision at one point along its length, takes a bridge 12 and inserts the pin 42 of bridge end 38 into the particular opening 46 in pressure strip 16 nearest to one exit point of the suture thread from the skin. The pin 42 on the other bridge end 40 is then aligned with an opening 46 on the other pressure strip 18 and inserted in it. The snug fit of the pins within the openings serves to mount the bridge 12 in position over the incision. The lower surface of bridge ends 38, 40 presents a shoulder which bears against the upper surface of each pressure strip. The enlarged configuration of each end serves to distribute the pressure of the bridge on the strip itself in addition to promoting the stability of the bridge as mounted. Referring to FIG. 3, the suture thread may be crossed beneath the bridge as shown and the ends passed through appropriate apertures 28 in the bottom wall 22 of bridge 12. Each end of the suture thread extending through the apertures is then looped around a respective post 32, 34 and knotted together as at 52 (FIG. 4). The thread is preferably looped around the posts several times prior to knotting to facilitate the splice and also to provide a reserve of suture material should the knot have to be cut during readjustment of the suture. The suture draws the opposed sides of incision 14 together to promote healing, and the arch-shaped configuration of bridge 12 permits easy accessibility to incision 14 and suture thread 30. The pressure exerted on the bridge by suture thread 30 is evenly transmitted by bridge ends 38, 40 to the pressure strips 16, 18 and evenly distributed over their relatively large area. As further suture loops are added along the length of the incision, additional bridges are mounted on the pressure strips and the pressure is transmitted from the ends of these bridges to the pressure strips which evenly distribute it over the relatively larger area.

The distance between opposed openings 46 on respective pressure strips 16, 18 defines a predetermined fixed distance equal to the distance between pins 42 on any one bridge. Each opening 50 laterally spaced relative to an adjacent opening 46 lies on an arc described through that opening 46 having a radius of curvature equal to the distance between the pins 42 on the bridge and whose center is the opposed opening 46 formed in the other pressure strip. For example, referring to FIG. 2 openings 100, 102 and 104 on pressure strip 18 all lie on the same arc having a radius of curvature R equal to the distance between pins 42 on a bridge with the center being opening 106 on strip 16. The reason for this structure is that occasionally the ends of the suture thread 30 exiting from the skin on either side of the incision are not precisely aligned with a pair of opposed openings 46 in respective pressure strips. In such circumstances, it is desirable to still have the bridge directly positioned over the suture loop. By so forming two sets of alternate openings 46, 50, the bridge 12 may be canted at an angle as illustrated by bridge 52 in FIG. 1 and still directly overlie the displaced suture loop.

Referring to FIGS. 5 through 8, another embodiment of a suture bridge is illustrated. The bridge 12' has substantially the same U-shaped cross section as bridge 12. Referring to FIG. 6, the bottom wall 22' has an arch-shaped cross section while apertures 28' are tapered upwardly. Such structure facilitates the threading of the suture thread 30 through the aperture since the bottom wall 22' tends to position the point of the needle towards the apex of the arch where the aperture is formed. In lieu of posts 32, 34 a knob 54 is provided, the knob being defined by a shaft 56 extending upwardly from bottom wall 22' terminating in an enlarged head 58. After the suture thread ends are passed through apertures 28', they are looped around shaft 56 and retained there by the shoulder 59 formed on the lower surface of head 58.

Obviously, numerous variations and modifications of the present invention are possible in light of the instant disclosure. For example, the pins and openings 42 and 44 respectively may be reversed so that the pressure strips have a series of upwardly extending pins while the bridge ends have openings formed in them. Other types of fasteners may be used to mount the bridge ends on the pressure strips. Further, the pressure distributing members may have different shapes than as shown and the openings 44 may be positioned otherwise than as shown. It is therefore to be understood that within the scope of the appended claims, the invention may be practiced otherwise than as specifically described herein.

What is claimed is:

1. A surgical bridge assembly for retention sutures looped about an incision in the skin comprising:

at least one bridge adapted to span said incision and terminating in first and second ends having respective first and second end surfaces, with first fastening means on said first end, and second fastening means on said second end;

first and second base means positionable on opposite sides of said incision, the lower surface of each having an area greater than that of said bridge end surfaces for distributing pressure exerted by said bridge ends over a surface area greater than that of said bridge end surfaces, said first base means having a plurality of third fastener means distributed over its surface in a general direction substantially transverse to the span of said bridge and said second base means having a plurality of fourth fastener means distributed over its surface in a general direction substantially transverse to the span of said bridge, said first and third fastener means and said second and fourth fastener means adapted to form respective releasable connections whereby said bridge may be attached to said base means at a plurality of points therealong.

2. A surgical bridge assembly according to claim 1 wherein each of said first and second base means comprises a substantially flat, flexible plastic member.

3. A surgical bridge assembly according to claim 1 wherein each of said base means comprises an elongate flexible strip adapted to be positioned on one side of said incision in generally parallel relationship therewith.

4. A surgical bridge assembly according to claim 1 wherein said fastener means are adapted to connect said bridge to said base means at any selected one of a plurality of angles therebetween as measured in a plane substantially parallel to said surfaces of said base means.

5. A surgical bridge assembly according to claim 1 wherein ones of said first and third fastening means and of said second and fourth fastening means comprise pin means and the others of said first and third and of said second and fourth fastening means comprise integral portions having openings adapted to snugly receive said pin means thereby releasably connecting the ends of said bridge to said respective base means.

6. A surgical bridge assembly according to claim 5 wherein the axes of said pin means and said openings are substantially transverse to said surfaces of said base means.

7. A surgical bridge assembly according to claim 1 wherein the distance between the first and second fastening means defines a radius of curvature and said pluralities of third and fourth fastener means are situated on said respective first and second base means so that the centers of ones of said third and fourth fastener means define respective first and second longitudinal axes on said respective first and second base means and the centers of others of said third and fourth fastener means are spaced from said respective first and second longitudinal axes so that when centers of particular ones of said third fastener means are separated by said radius of curvature from centers of particular ones of said fourth fastener means, the centers of some others of said fourth fastener means are also separated by said radius of curvature from said particular ones of said third fastener means and the centers of some others of said third fastener means are separated by said radius of curvature from said particular ones of said fourth fastener means.

8. A surgical bridge assembly as recited in claim 1 wherein said at least one bridge has a U-shaped configuration having spaced apertures formed along its length for passing suture thread therethrough.

9. A surgical bridge assembly as recited in claim 1 wherein said at least one bridge includes means for securing the ends of said suture thread after it has been looped around said incision.

10. A surgical bridge assembly as recited in claim 1 wherein said bridge has a substantially U-shaped cross-section.

11. A surgical bridge assembly according to claim 1 wherein said first and second fastener means and wherein said third and fourth fastener means are substantially identical.

* * * * *